(12) United States Patent
Liu et al.

(10) Patent No.: US 7,017,416 B1
(45) Date of Patent: Mar. 28, 2006

(54) DISPOSABLE PRESSURE DIAPHRAGM AND WIRELESS SENSOR SYSTEMS AND METHODS

(75) Inventors: James Z. Liu, Rockford, IL (US); James D. Cook, Freeport, IL (US); Peter P. Dierauer, Freeport, IL (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 10/972,260

(22) Filed: Oct. 22, 2004

(51) Int. Cl.
*G01L 11/00* (2006.01)

(52) U.S. Cl. ..................................... 73/702
(58) Field of Classification Search ............... 73/715, 73/700, 702
See application file for complete search history.

(56) References Cited

U.S. PATENT DOCUMENTS

| | | | | |
|---|---|---|---|---|
| 4,454,440 A | * | 6/1984 | Cullen | 310/313 R |
| 5,155,708 A | | 10/1992 | Bedi et al. | 367/152 |
| 5,821,425 A | | 10/1998 | Mariani et al. | 73/703 |
| 5,853,020 A | * | 12/1998 | Widner | 137/227 |
| 6,170,318 B1 | | 1/2001 | Lewis | 73/23.34 |
| 6,314,791 B1 | | 11/2001 | Rapp et al. | 73/24.06 |
| 6,331,244 B1 | | 12/2001 | Lewis et al. | 205/777.5 |
| 6,508,129 B1 | | 1/2003 | Sittler | 73/756 |
| 6,520,020 B1 | | 2/2003 | Lutz et al. | 73/706 |
| 6,571,638 B1 | | 6/2003 | Hines et al. | 73/702 |
| 6,640,613 B1 | | 11/2003 | Rapp et al. | 73/24.01 |
| 6,710,515 B1 | | 3/2004 | Lu et al. | 310/313 |
| 6,865,950 B1 | * | 3/2005 | Leigh et al. | 73/702 |
| 6,907,787 B1 | * | 6/2005 | Cook et al. | 73/700 |
| 2002/0113521 A1 | | 8/2002 | Rapp et al. | 310/313 R |
| 2003/0196477 A1 | | 10/2003 | Auner et al. | 73/24.06 |

* cited by examiner

*Primary Examiner*—Edward Lefkowitz
*Assistant Examiner*—Andre Allen
(74) *Attorney, Agent, or Firm*—Kermit D. Lopez; Luis M. Ortiz

(57) ABSTRACT

A disposable and wireless sensor system and method are disclosed. In general, a pressure diaphragm can be connected to one or more reusable Surface Acoustic Wave (SAW) probe heads, which are associated with an antenna for wirelessly receiving or transmitting signals that excite the reusable SAW probe head only when the reusable SAW head is in contact with the pressure diaphragm. Interrogation electronics can also be provided, which are associated with the reusable SAW probe head. One or more signals can be wirelessly transmitted to the interrogation electronics for exciting the reusable SAW probe head for pressure sensing applications thereof.

21 Claims, 2 Drawing Sheets

DISPOSABLE PRESSURE DIAPHRAGM AND WIRELESS SENSOR SYSTEMS AND METHODS

TECHNICAL FIELD

Embodiments are generally related to sensing devices and applications. Embodiments are also related to pressure sensor devices, systems and methods thereof. Embodiments are additionally related to disposable sensing devices and surface acoustic wave (SAW) devices.

BACKGROUND OF THE INVENTION

A variety of sensors are utilized to detect conditions, such as pressure and temperature. The ability to detect pressure and/or temperature is an advantage to any device exposed to variable pressure conditions, which can be severely affected by these conditions. An example of such a device is a catheter, which of course, can experience variations in both temperature and pressure. Many different techniques have been proposed for sensing the pressure and/or temperature in catheters, and for delivering this information to an operator so that he or she is aware of pressure and temperature conditions associated with a catheter and any fluid, such as blood flowing therein.

One type of sensor that has found wide use in pressure and temperature sensing applications is the Surface Acoustic Wave (SAW) sensor, which can be composed of a sense element on a base and pressure transducer sensor diaphragm that is part of the cover. For a SAW sensor to function properly, the sensor diaphragm should generally be located in intimate contact with the sense element at all pressure levels and temperatures.

One of the problems with current SAW sensor designs, particularly those designs adapted to delicate pressure and temperature sensing applications, is the inability of conventional SAW sensing systems to meet the demand in low pressure applications. (e.g., 0 to 500 mmHg), while doing so in an efficient and low cost manner. Such systems are inherently expensive, awkward, and often are not reliable in accurately sensing tire air pressure and temperature. There is a continuing need to lower the cost of SAW sensor designs utilized in pressure and/or temperature sensing applications, particularly wireless pressure sensors.

To lower the cost and raise efficiency, few components, less expensive materials and fewer manufacturing-processing steps are necessary. In order to achieve these goals, it is believed that a disposable pressure sensor diaphragm should be implemented, along with reusable wireless transducers. To date, such components have not been achieved. It is therefore believed that a solution to such problems involves a disposable low cost SAW sensor packaging system, which can be integrated into a catheter and interrogated wirelessly. Such a system is described in greater detail herein.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved sensing devices and applications.

It is another aspect of the present invention to provide for improved pressure sensor devices, systems and methods thereof.

It is a further aspect of the present invention to provide for an improved and disposable pressure diaphragm utilized in a Surface Acoustic Wave (SAW) sensing device.

It is an additional aspect of the present invention to provide for a pressure sensor system that includes a SAW sensing device, a pressure diaphragm and interrogation electronics for wirelessly detecting pressure conditions associated with a catheter.

The aforementioned aspects of the invention and other objectives and advantages can now be achieved as described herein. A disposable and wireless sensor system and method are disclosed. In general, a pressure diaphragm can be connected to one or more reusable Surface Acoustic Wave (SAW) probe heads, which are associated with an antenna for wirelessly receiving or transmitting signals that excite the reusable SAW probe head only when the reusable SAW head is in contact with the pressure diaphragm. Interrogation electronics can also be provided, which are associated with the reusable SAW probe head. One or more signals can be can be wirelessly transmitted to the interrogation electronics for exciting the reusable SAW probe head for pressure sensing applications thereof.

Additionally, an iron ring can be provided, which surrounds the reusable SAW probe head. The iron ring can initiate a switch via a magnetic force when the pressure diaphragm and the reusable SAW probe head contact one another so that the switch connects the reusable SAW probe head to the antenna and thereby excite the reusable SAW probe head via the interrogation electronics.

The reusable SAW probe head can be magnetically connected mechanically connected and/or connected via a vacuum to the pressure diaphragm. A low thermal conductivity material can be utilized to form the pressure diaphragm, which can further be formed in a corrugated shape or bossed shape for improved linearity. The pressure diaphragm can also be formed from a biocompatible material and located proximate to and on a catheter through which a fluid flows. The pressure diaphragm itself can be configured as a disposable pressure diaphragm.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
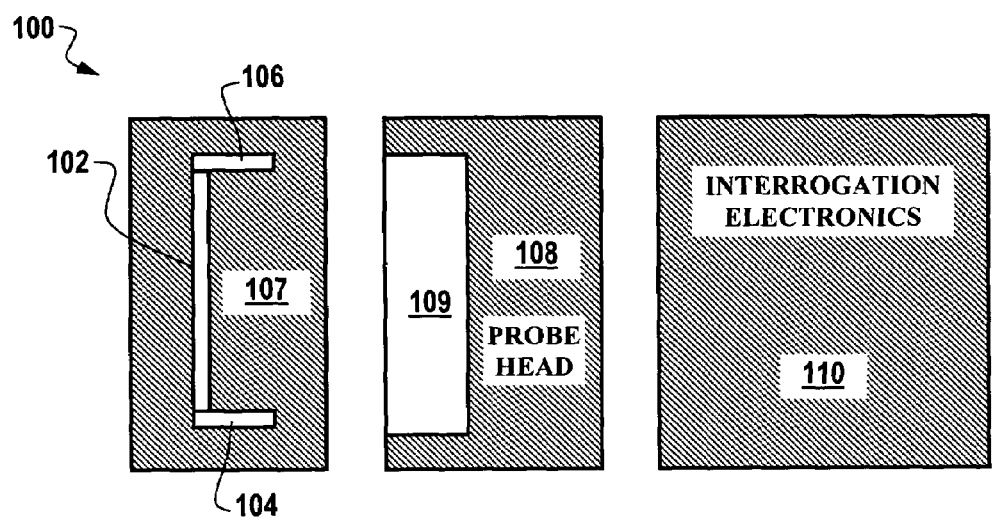
FIG. 1 illustrates a block diagram of a wireless pressure diaphragm and sensor system, which can be implemented in accordance with a preferred embodiment.

FIG. 1 illustrates a block diagram of a wireless pressure diaphragm 102 and sensor system 100, which can be implemented in accordance with a preferred embodiment. In general, system 100 includes a probe guide 104 and a probe guide 106, which are located proximate to pressure diaphragm 102 within a catheter area 107 of a catheter. A multiple use wireless probe head 109 can be located within an area 108, such that probe head 109 communicates with interrogation electronics 110.

The connection of the pressure diaphragm 102 to the probe head 109 can be performed magnetically, mechanically, or through the use of a vacuum (e.g., a vacuum "sucking" on pressure diaphragm 102). One or more signals from the probe head 109 can be transferred wirelessly to interrogation electronics 110. Pressure can be transferred through direct contact, silicone gel, hydraulically, and the like. The magnetic connection can be accomplished through the use of a magnetic force at the pressure diaphragm 102 or at the border of pressure diaphragm 102 on the catheter (e.g., catheter area 107).

The pressure diaphragm 102 can be configured with a corrugated shape or bossed shape for improved linearity, and may be formed from materials with a low thermal conductivity, if blood or analytes flowing through catheter area 107 possess a large temperature difference with ambient temperature and/or if the pressure mechanism itself (i.e., pressure diaphragm 102) is sensitive to temperature. The pressure diaphragm 102 can be located on the side, top or bottom of catheter area 107 depending upon design considerations. The pressure diaphragm 102 is preferably formed from a biocompatible material. The polymeric biomaterials for this application can include, but is not limited to, polyvinylchloride (PVC), polyethylene (PE), polypropylene (PP), polymethymetacrylate (PMMA), polystyrene (PS), polyethylenterephthalate (PET), polytetrafluoroethylene (PTFE), polyurethane (PU), polyamide (Nylon), and so forth.

Figure 2:
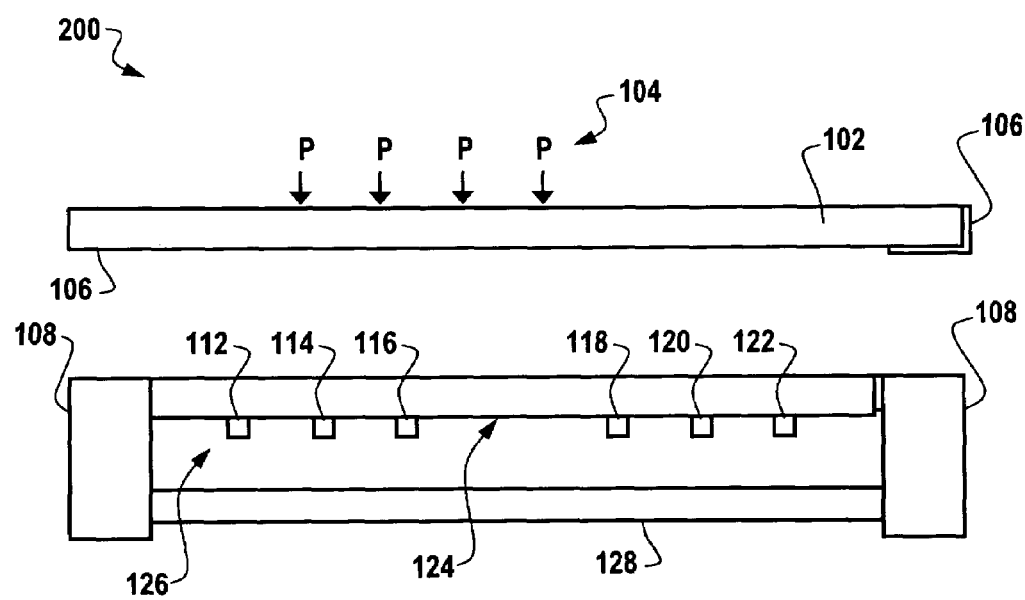
FIG. 2 illustrates a block diagram of a wireless pressure diaphragm and sensor system that includes an iron ring and a ring type magnet, in accordance with a preferred embodiment.

FIG. 2 illustrates a block diagram of a wireless pressure diaphragm 102 and sensor system 200 that includes an iron ring 106 and a ring type magnet 108 in association, in accordance with a preferred embodiment. The system 200 depicted in FIG. 2 can be implemented in association with the system 100 illustrated in FIG. 1. Note that in FIGS. 1–4 identical or similar parts or elements are generally indicated by identical reference numerals.

Pressure is indicated in system 200 by arrows 104. Pressure diaphragm 102 is located proximate and opposite to ring type magnet 108 and a sensing device 124 that can be, for example, a piezoelectric membrane, a SAW device, or a device that includes a plurality of interdigital transducers (IDT's) 112, 114, 116, 118, 120, 122. A wireless probe head 126 can therefore be formed from device 124 and IDT's 112, 114, 116, 118, 120, 122. Depending on the piezo-electric coupling coefficient, some portion of the piezoelectric device substrate (with low coupling coefficient) may need to be etched. The etched area can be filled with gel type materials for pressure transfer capabilities.

Probe head 126 can therefore be implemented as a SAW probe head. When the probe head 126 and the pressure diaphragm 102 are in contact with one another, iron ring 106 can push a switch (not shown in FIG. 2) into an "on" position by a magnetic force associated with magnet 108. Such a switch can connect the SAW probe head 126 and an antenna 128 in order to excite the SAW probe head 126 via the interrogation electronics depicted in FIG. 1.

Figure 3:
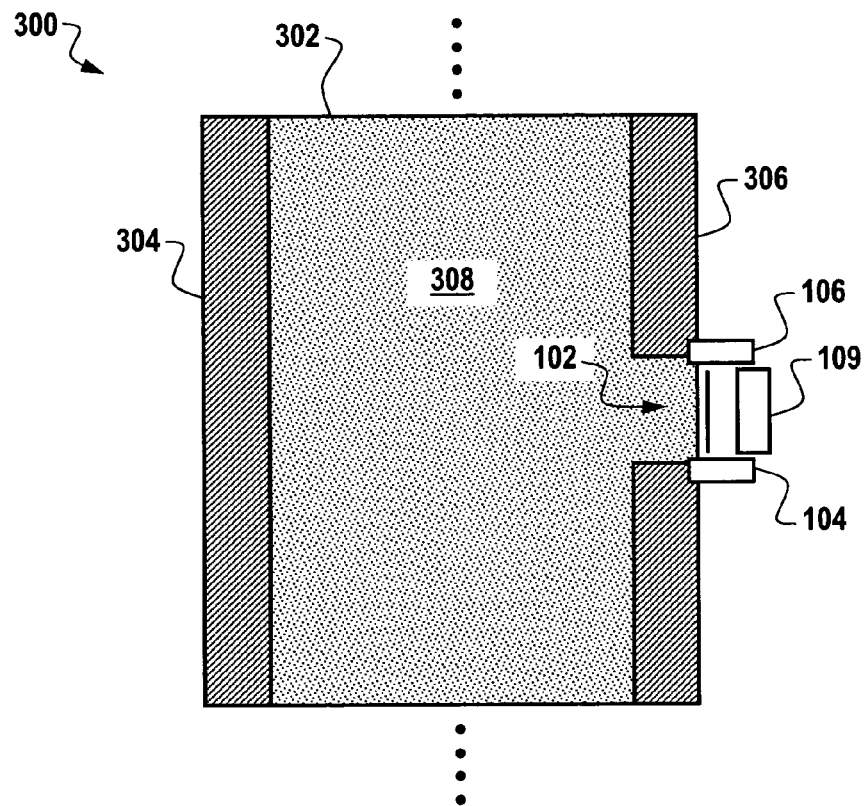
FIG. 3 illustrates a block diagram of a wireless pressure diaphragm and sensor system, including a catheter in association with a pressure diaphragm, probe heads and a probe guide, in accordance with a preferred embodiment.

FIG. 3 illustrates a block diagram of a wireless pressure diaphragm 102 and sensor system 300, including a catheter 302 in association with pressure diaphragm 102, probe guide 104, 106 and a probe head 109, in accordance with a preferred embodiment. Fluid 308, such as, for example, can flow through catheter 302. Note that catheter 302 is generally analogous to catheter area 107 discussed above with respect to FIG. 1. Catheter 302 includes catheter walls 304, 306. Pressure diaphragm 102 can be molded in catheter 302.

The magnet 108 and the SAW device 124 together can form a single reusable SAW probe head 109. It can be appreciated that system 300 depicted in FIG. 3 can be equipped with multiple SAW probe heads, depending upon design considerations, in accordance with alternative embodiments. Note that antenna 128 depicted in FIG. 3 can be implemented in accordance with the configuration illustrated in FIG. 3 and can be in contact with SAW probe head 109 when such probe head is in contact with pressure diaphragm 102. Care should be taken to ensure that SAW probe head 109 is excited only when it is in contact with pressure diaphragm 102.

Figure 4:
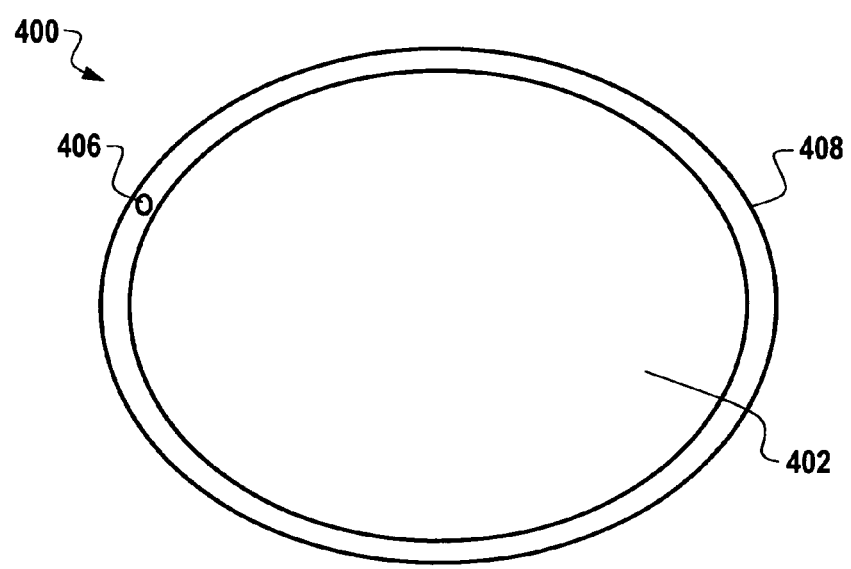
FIG. 4 illustrates a block diagram of a probe head that can be implemented in accordance with a preferred embodiment.

FIG. 4 illustrates a block diagram of a probe head 400 that can be implemented in accordance with a preferred embodiment. Note that probe head 400 depicted in FIG. 4 is generally analogous to SAW probe head 109 discussed above. Probe head 400 generally possesses a circular shape, and includes a SAW, IDT or piezoelectric area 402, which is surrounded by an iron ring 408. Note that the iron ring 408 depicted in FIG. 4 is analogous to the iron ring 106 discussed above with respect to FIG. 2. Thus, iron ring 408 can be utilized to implement iron ring 106. An auto-0 (zero) button 406 can be disposed on iron ring 408. A magnet area (not shown in FIG. 4) can contact iron ring 408.

Note that when the sensor is connected to the pressure diaphragm, and before the catheter experiences any pressure, the sensor response shift is due to ambient temperature and ambient pressure change (around 760 mmHg). This shift should not be considered as sensor response, and will be counted as "zero". This is addressed by auto-0 button 406. When the antenna is connected to the SAW device, the interrogation will be able to receive a response. This initial response is considered as "0". Before the switch is on, however, when antenna is not connected with SAW, there will be very little or no signal from the SAW.

Based on the foregoing, it can be appreciated that a disposable and wireless sensor system and method are disclosed. In general, a pressure diaphragm can be connected to a reusable Surface Acoustic Wave (SAW) probe head with one or more SAW sensors, which are associated with an antenna for wirelessly receiving or transmitting signals that excite the reusable SAW probe head only when the reusable SAW head is in contact with the pressure diaphragm. Interrogation electronics can also be provided, which are associated with the reusable SAW probe head. One or more signals can be can be wirelessly transmitted to the interrogation electronics for exciting the reusable SAW probe head for pressure sensing applications thereof.

Additionally, a magnetic ring can be provided, which surrounds the reusable SAW probe head. The ring magnet (on the probe head) and the iron ring (on the diaphragm) can initiate a switch via a magnetic force when the pressure diaphragm and the reusable SAW probe head contact one another so that the switch connects the reusable SAW probe head to the antenna and thereby excite the reusable SAW probe head via the interrogation electronics.

The reusable SAW probe head can be magnetically connected mechanically connected and/or connected via a vacuum to the pressure diaphragm. A low thermal conductivity material can be utilized to form the pressure diaphragm, which can further be formed in a corrugated shape or bossed shape for improved linearity. The pressure diaphragm can also be formed from a biocompatible material and located proximate to and on a catheter through which a fluid flows. The pressure diaphragm itself can be configured as a disposable pressure diaphragm.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A disposable sensor system, comprising:
   a pressure diaphragm connected to at least one reusable Surface Acoustic Wave (SAW) probe head associated with an antenna for wirelessly receiving or transmitting signals, which excite said at least one reusable SAW probe head only when said at least one reusable SAW head is in contact with said pressure diaphragm;
   interrogation electronics associated with said at least one reusable SAW probe head, wherein a signal from said at least one reusable SAW probe head can be wirelessly transmitted to said interrogation electronics for exciting said at least one reusable SAW probe head for pressure sensing applications thereof; and
   an iron ring that surrounds said at least one reusable SAW probe head, wherein said iron ring initiates a switch via a magnetic force when said pressure diaphragm and said at least one reusable SAW probe head contact one another so that said switch connects said at least one reusable SAW probe head to said antenna and thereby excite said at least one reusable SAW probe head via said interrogation electronics.

2. The system of claim 1 wherein said at least one reusable SAW probe head is connected magnetically to said pressure diaphragm via a magnetic force.

3. The system of claim 1 wherein said at least one reusable SAW probe head is connected mechanically to said pressure diaphragm.

4. The system of claim 1 wherein said at least one reusable SAW probe head is connected to said pressure diaphragm via a vacuum force.

5. The system of claim 1 wherein said pressure diaphragm comprises a low thermal conductivity material.

6. The system of claim 1 wherein said pressure diaphragm comprises a corrugated shape for improved linearity.

7. The system of claim 1 wherein said pressure diaphragm comprises a bossed shape for improved linearity.

8. The system of claim 1 wherein said pressure diaphragm comprises a biocompatible material and is located proximate to and on a catheter through which a fluid flows.

9. The system of claim 1 wherein said pressure diaphragm comprises a disposable pressure diaphragm.

10. A disposable sensor system, comprising:
    a disposable pressure diaphragm magnetically connected to at least one reusable Surface Acoustic Wave (SAW) probe head associated with an antenna for wirelessly receiving or transmitting signals, which excite said at least one reusable SAW probe head only when said at least one reusable SAW head is in contact with said disposable pressure diaphragm;
    interrogation electronics associated with said at least one reusable SAW probe head, wherein a signal from said at least one reusable SAW probe head can be wirelessly transmitted to said interrogation electronics for exciting said at least one reusable SAW probe head for pressure sensing applications thereof; and
    a ring magnet that surrounds said at least one reusable SAW probe head, wherein said ring magnet and an iron ring located on pressure diaphragm initiates a switch via a magnetic force when said disposable pressure diaphragm and said at least one reusable SAW probe head contact one another so that said switch connects said at least one reusable SAW probe head to said antenna and thereby excite said at least one reusable SAW probe head via said interrogation electronics; and
    a catheter through which fluid flows, wherein said pressure diaphragm is located at and molded to said catheter in order to permit sensing of pressure on or within said catheter by said SAW probe head.

11. The system of claim 10 wherein said pressure diaphragm comprises a biocompatible material.

12. The system of claim 10 wherein said fluid flowing through said catheter comprises blood.

13. The system of claim 10 wherein said pressure diaphragm is formed from a low thermal conductivity material.

14. The system of claim 10 wherein said pressure diaphragm comprises a corrugated shape for improved linearity.

15. A disposable sensor method, comprising the steps of:
    connecting a disposable pressure diaphragm to at least one reusable Surface Acoustic Wave (SAW) probe head associated with an antenna for wirelessly receiving or transmitting signals, which excite said at least one reusable SAW probe head only when said at least one reusable SAW head is in contact with said disposable pressure diaphragm;
    associating interrogation electronics with said at least one reusable SAW probe head, wherein a signal from said at least one reusable SAW probe head can be wirelessly transmitted to said interrogation electronics for exciting said at least one reusable SAW probe head for pressure sensing applications thereof; and
    surrounding said at least one reusable SAW probe head with said ring magnet, wherein said ring magnet and an iron ring located on pressure diaphragm initiates a switch via a magnetic force when said disposable pressure diaphragm and said at least one reusable SAW probe head contact one another so that said switch connects said at least one reusable SAW probe head to said antenna and thereby excite said at least one reusable SAW probe head via said interrogation electronics.

16. The method of claim 15 wherein the step of connecting a disposable pressure diaphragm to at least one reusable SAW probe head, further comprises the step of:
   magnetically connecting said disposable pressure diaphragm to said at least one reusable SAW probe head via a magnetic force.

17. The method of claim 15 wherein the step of connecting a disposable pressure diaphragm to at least one reusable SAW probe head, further comprises the step of:
   mechanically connecting said disposable pressure diaphragm to said at least one reusable SAW probe head.

18. The method of claim 15 wherein the step of connecting a disposable pressure diaphragm to at least one reusable SAW probe head, further comprises the step of:
   connecting said disposable pressure diaphragm to said at least one reusable SAW probe via a vacuum force.

19. The method of claim 15 further comprising the step of forming said disposable pressure diaphragm from a low thermal conductivity material.

20. The method of claim 15 further comprising the step of configuring said disposable pressure diaphragm in a corrugated shape for improved linearity.

21. The method of claim 15 further comprising the steps of:
   forming said disposable pressure diaphragm from a biocompatible material;
   locating said disposable pressure diaphragm proximate to and on a catheter through which a fluid flows; and
   molding said disposable pressure diaphragm in said catheter.

* * * * *